(12) United States Patent
Mukai et al.

(10) Patent No.: US 10,729,596 B2
(45) Date of Patent: Aug. 4, 2020

(54) PANTS-TYPE ABSORBENT ARTICLE

(71) Applicant: UNICHARM CORPORATION, Shikokuchuo-shi, Ehime (JP)

(72) Inventors: Hirotomo Mukai, Kanonji (JP); Akihide Ninomiya, Kanonji (JP); Akihisa Shiomi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 432 days.

(21) Appl. No.: 15/580,682

(22) PCT Filed: May 25, 2016

(86) PCT No.: PCT/JP2016/065520
§ 371 (c)(1),
(2) Date: Dec. 7, 2017

(87) PCT Pub. No.: WO2016/199581
PCT Pub. Date: Dec. 15, 2016

(65) Prior Publication Data
US 2018/0185203 A1 Jul. 5, 2018

(30) Foreign Application Priority Data
Jun. 8, 2015 (JP) .................................. 2015-116118

(51) Int. Cl.
*A61F 13/49* (2006.01)
*A61F 13/496* (2006.01)
(Continued)

(52) U.S. Cl.
CPC ...... *A61F 13/496* (2013.01); *A61F 13/15203* (2013.01); *A61F 13/49001* (2013.01);
(Continued)

(58) Field of Classification Search
CPC ................ A61F 13/49; A61F 13/49011; A61F 13/49012; A61F 13/4906; A61F 13/49061;
(Continued)

(56) References Cited

U.S. PATENT DOCUMENTS 7,806,885 B2* 10/2010 Inoue ...................... A61F 13/84
604/378
8,840,600 B2* 9/2014 Takeuchi .......... A61F 13/49011
604/385.3
(Continued)

FOREIGN PATENT DOCUMENTS

JP 2001-61890 A 3/2001
JP 2009-297299 A 12/2009
(Continued)

OTHER PUBLICATIONS

Extended European Search Report in EP Application No. 16807288.2, dated May 16, 2018, 6pp.
(Continued)

*Primary Examiner* — Catharine L Anderson
(74) *Attorney, Agent, or Firm* — Hauptman Ham, LLP

(57) ABSTRACT

A pants-type absorbent article for which damage during wearing motions can be suppressed. The pants-type absorbent article includes: a front waist region; a rear waist region; a crotch region; a waist opening defined by the front waist region and the rear waist region and disposed to surround a waist of the wearer; an external topsheet provided on at least one of the front waist region and the rear waist region; and an external backsheet bonded to the external topsheet. The external backsheet has a folded-back portion folded back at the waist opening, the folded-back portion extending beyond the external topsheet toward to the waist opening. A reinforcing sheet extends in a transverse direction orthogonally crossing the front-back direction and
(Continued)

to overlap at least part of the folded-back portion. The reinforcing sheet has a length in the front-back direction longer than a length of the folded-back portion in the front-back direction.

9 Claims, 4 Drawing Sheets

(51) Int. Cl.
*A61F 13/514* (2006.01)
*A61F 13/15* (2006.01)
*A61F 13/515* (2006.01)

(52) U.S. Cl.
CPC .. *A61F 13/49011* (2013.01); *A61F 13/51458* (2013.01); *A61F 13/51476* (2013.01); *A61F 13/51478* (2013.01); *A61F 13/51498* (2013.01); *A61F 13/515* (2013.01); *A61F 2013/15357* (2013.01); *A61F 2013/15406* (2013.01); *A61F 2013/15552* (2013.01); *A61F 2013/51494* (2013.01)

(58) Field of Classification Search
CPC .............. A61F 13/49466; A61F 13/496; A61F 2013/49025; A61F 2013/49026; A61F 2013/49486

See application file for complete search history.

(56) References Cited

U.S. PATENT DOCUMENTS

| | | | |
|---|---|---|---|
| 9,498,393 B2 * | 11/2016 | Fukasawa | ......... A61F 13/49011 |
| 2009/0157029 A1 | 6/2009 | Hornung et al. | |
| 2017/0281421 A1 * | 10/2017 | Umemoto | ............... A61F 13/49 |

FOREIGN PATENT DOCUMENTS

| | | |
|---|---|---|
| JP | 2013-128512 A | 7/2013 |
| JP | 2013-172861 A | 9/2013 |
| JP | 2013-223688 A | 10/2013 |
| JP | 2014-188189 A | 10/2014 |
| WO | 2011/122604 A1 | 10/2011 |

OTHER PUBLICATIONS

International Search Report in PCT/JP2016/065520, dated Jul. 5, 2016.

* cited by examiner

PANTS-TYPE ABSORBENT ARTICLE

RELATED APPLICATIONS

The present application is a national phase of International Application Number PCT/JP2016/065520, filed May 25, 2016, which claims priority to JP2015-116118, filed Jun. 8, 2015.

TECHNICAL FIELD

The present invention relates to pants-type absorbent articles.

BACKGROUND ART

Patent Literature 1 discloses a pants-type absorbent article. The absorbent article includes a front waist region disposed on the abdominal part of a wearer, a rear waist region disposed on the back part of the wearer, and a crotch region corresponding to the crotch of the wearer located between the front waist region and the rear waist region. The front waist region and the rear waist region form a waist opening through which the waist portion of the wearer is inserted. The absorbent article includes an absorbent body having an absorber placed therein, and an exterior part disposed outside the absorbent body. The exterior part is at least provided in the front waist region and the rear waist region. The exterior part is folded inward at end portions on the waist opening side.

CITATION LIST

Patent Literature

Patent Literature 1: JP2013-128512 A

SUMMARY

The object of Patent Literature 1 is to improve air permeability in the front and rear waist regions. One method that can be considered to improve the air permeability is to decrease a thickness of an exterior member, that is, to decrease a basis weight of the exterior member. Decreasing the basis weight of the exterior member is preferable also in terms of cost reduction. However, a thinner exterior member would cause breakage of the pants-type absorbent article when worn and while the wearer is active.

In view of the above, it is desired to provide a pants-type absorbent article capable of preventing breakage when worn and while the wearer is active even when the exterior member is thin.

According to an embodiment, a pants-type absorbent article comprises: a front waist region to be placed on a front waist of a wearer; a rear waist region to be placed on a rear waist of the wearer; a crotch region located between the front waist region and the rear waist region; a front-back direction extending from the front waist region to the rear waist region; a waist opening defined by the front waist region and the rear waist region and disposed to surround a waist of the wearer; an external topsheet provided on at least one of the front waist region and the rear waist region; and an external backsheet bonded to the external topsheet. The external backsheet has a folded-back portion folded back at the waist opening, the folded-back portion extending beyond the external topsheet toward to the waist opening. A reinforcing sheet is provided to extend in a transverse direction orthogonally crossing the front-back direction and to overlap at least part of the folded-back portion. The reinforcing sheet has a length in the front-back direction longer than a length of the folded-back portion in the front-back direction.

DESCRIPTION OF EMBODIMENTS

Figure 1:
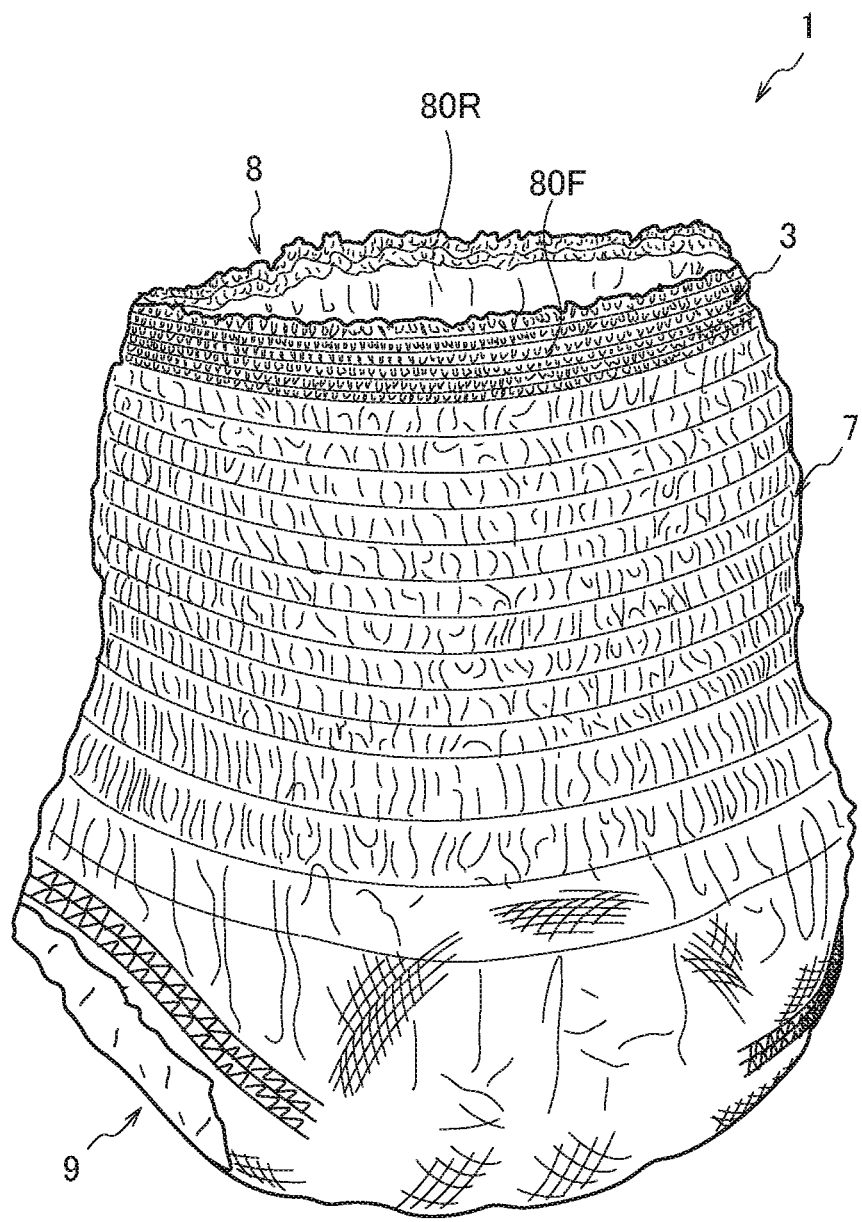
FIG. 1 is a perspective view of a disposable diaper according to an embodiment.

An absorbent article according to an embodiment will be described by referring to the accompanying drawings. The absorbent article according to the present embodiment is a disposable diaper. In the drawings, the same or similar parts are indicated by the same or similar reference symbols. The drawings are illustrated schematically, and dimensional ratios and other variables differ from those of actual measurements.

The specific measurements or the like, therefore, should be determined by referring to the following description. The drawings may have different dimensional relations or ratios.

(1) Structure of Disposable Diaper

Figure 2:
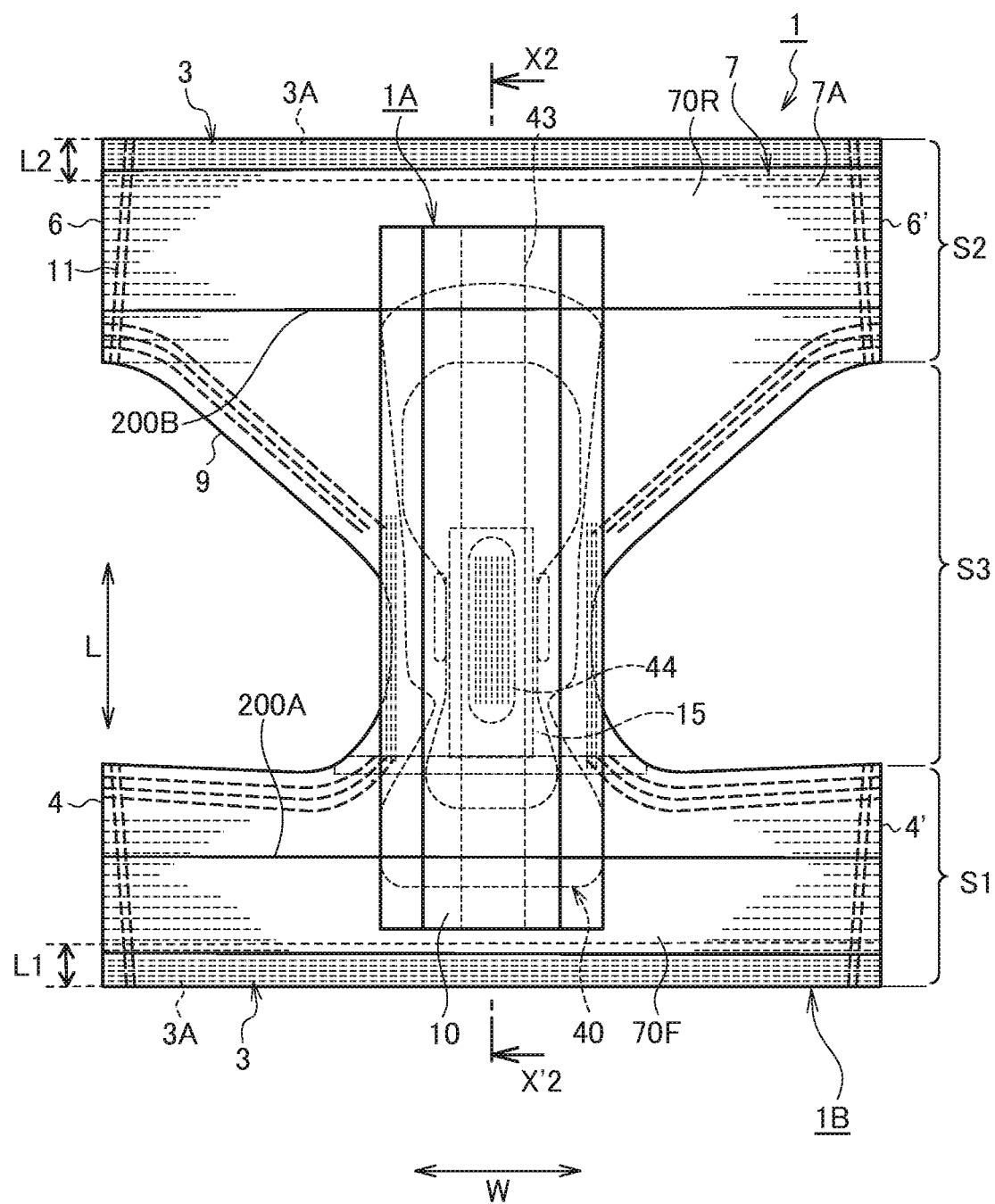
FIG. 2 is an exploded plan view of the disposable diaper according to the embodiment.

FIG. 1 is a plan view of an absorbent article according to an embodiment. FIG. 2 is a cross-sectional view of the absorbent article of FIG. 1 cut along line F2-F2. The absorbent product of the present embodiment is a disposable diaper.

Figure 3:
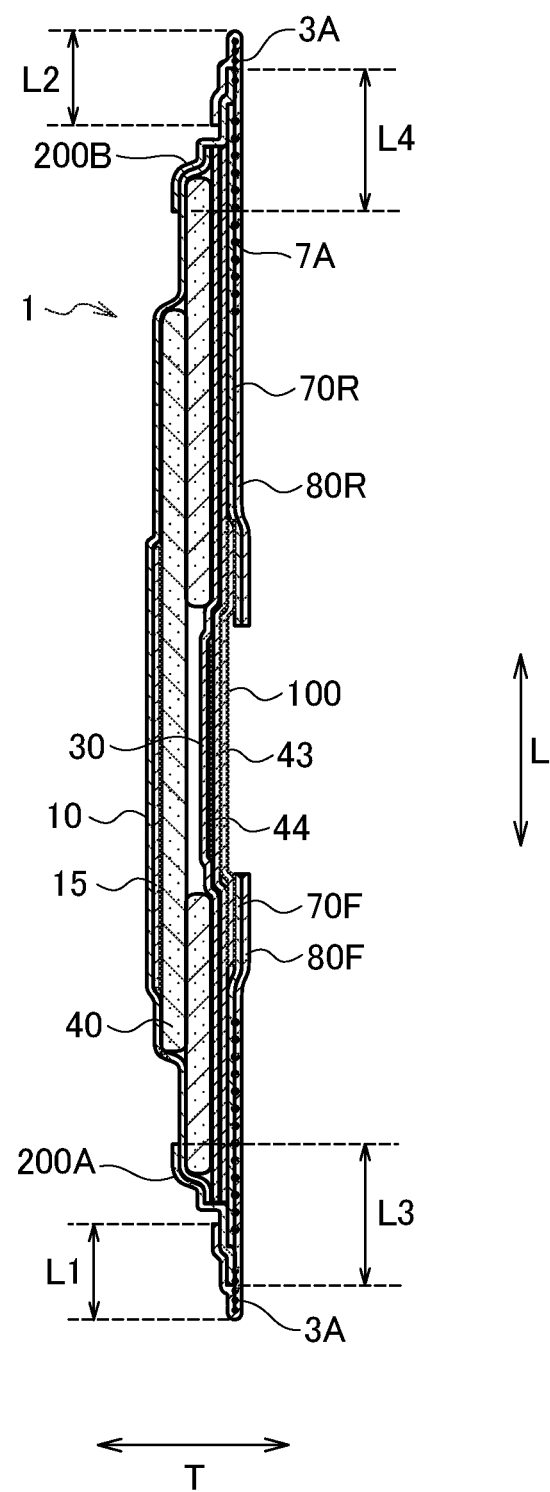
FIG. 3 is a cross-sectional view of the disposable diaper of FIG. 2 cut along line X2-X'2 according to the embodiment.

FIG. 1 is a schematic perspective view of a disposable diaper 1 according to the embodiment. FIG. 2 is an exploded plan view of the disposable diaper 1 according to the present embodiment. FIG. 3 is a cross-sectional view of the disposable diaper 1 of FIG. 2 cut along line X2-X'2. The disposable diaper 1 may be a pants-type disposable diaper.

As illustrated in FIG. 2, the disposable diaper 1 includes a front waist region S1 to be placed on the front waist of a wearer, a rear waist region S2 to be placed on the rear waist of the wearer, and a crotch region S3 to be placed on the crotch of the wearer and located between the front waist region S1 and the rear waist region S2.

The disposable diaper 1 has a front-back direction L extending between the front side and the rear side of the body of the wearer and a transverse direction W orthogonally crossing the front-back direction L, and a thickness direction T extending in an inward direction toward the wearer and an outward direction opposite to the inward direction. In other words, the front-back direction L is a direction extending from the front waist region S1 toward the rear waist region S2.

Front waist edge portions 4, 4' located outside the front waist region S1 in the transverse direction W of the front waist region S1 are bonded, respectively, to rear waist edge portions 6, 6' located outside the rear waist region S2 in the transverse direction W, whereby the disposable diaper 1 is formed into a pants shape. The front waist region S1 and the rear waist region S2 of the pants-type disposable diaper 1 each have a bonded portion 11 at which edges of both regions are bonded. The crotch region S3 is a region inside the bonded portion 11 in the front-back direction L.

As illustrated in FIG. 1, the disposable diaper 1 is formed into a pants shape and has a waist opening 8 surrounding the waist of the wearer and a pair of leg openings 9 each surrounding a leg of the wearer. The waist opening 8 is defined by the front waist region S1 and the rear waist region S2.

The disposable diaper 1 may include an absorbent body 1A and an exterior member 1B. The absorbent body 1A and the exterior member 1B are bonded with an adhesive or by heat-sealing. The absorbent body 1A is disposed closer to the skin side of the wearer than the exterior member 1B is. The absorbent body 1A may include a surface sheet 10, an absorber 40, and an absorber backsheet 30.

The surface sheet 10 is a sheet that forms a skin-abutting surface that can directly touch the skin of the wearer. The surface sheet 10 is disposed closer to the skin-abutting surface than the absorber 40 is. The surface sheet 10 may be made of a liquid-permeable sheet, such as hydrophilic nonwoven or woven fabric, a porous plastic film, or porous hydrophobic nonwoven fabric.

The absorbent body 1A may include a second sheet 15 provided on the non-skin-abutting surface side of the surface sheet 10. The second sheet 15 may be disposed between the surface sheet 10 and the absorber 40.

The absorber 40 is provided at least in the crotch region S3. The absorber 40 is provided between a compound sheet, which is formed by bonding the surface sheet 10 to the second sheet 15, and the absorber backsheet 30. The absorber 40 may be bonded to the compound sheet and the absorber backsheet 30 with a hot-melt adhesive. The absorber 40 is made of mixed powder, such as crushed pulp or superabsorbent polymer.

The absorber backsheet 30 is provided on the non-skin-abutting surface side of the absorber 40. The absorber backsheet 30 may be made of a liquid impermeable sheet. The absorber backsheet 30 is disposed outside the absorber 40 and has a liquid-impermeable characteristic. The absorber backsheet 30 is disposed extending farther in the front-back direction L than the absorber 40 is.

The exterior member 1B forms an exterior member of the disposable diaper 1. The exterior member 1B is located outside the absorbent body 1A which includes the absorber 40, and is disposed on the non-skin-abutting side surface of the disposable diaper 1. The exterior member 1B includes a front external topsheet 70F, a rear external topsheet 70R, a front external backsheet 80F, a rear external backsheet 80R, and an external center sheet 100. The front external topsheet 70F and the front external backsheet 80F are disposed at least in the front waist region S1. The rear external topsheet 70R and the rear external backsheet 80R are disposed at least in the rear waist region S2.

The front external topsheet 70F may be disposed over the front waist region S1 and the crotch region S3. The rear external topsheet 70R may be disposed over the rear waist region S2 and the crotch region S3. The front external topsheet 70F and the rear external topsheet 70R may be separated from each other in the front-back direction L. The front external topsheet 70F is disposed between the front external backsheet 80F and the absorbent body 1A. The front external topsheet 70F and the front external backsheet 80F are bonded together. The rear external topsheet 70R is disposed between the rear external backsheet 80R and the absorbent body 1A. The rear external topsheet 70R and the rear external backsheet 80R are bonded together. The front external topsheet 70F and the rear external topsheet 70R may be made of, for example, air-through nonwoven fabric, spunbond nonwoven fabric, SMS nonwoven fabric, or a water-resistant film. The front external backsheet 80F and the rear external backsheet 80R may be made of, for example, air-through nonwoven fabric, spunbond nonwoven fabric, SMS nonwoven fabric, or a water-resistant film.

The front external backsheet 80F and the rear external backsheet 80R are located on the exterior when worn or disposed far from the skin of the wearer. The front external backsheet 80F is disposed over the front waist region S1 and the crotch region S3. The rear external backsheet 80R is disposed over the rear waist region S2 and the crotch region S3. The front external backsheet 80F and the rear external backsheet 80R may be separated from each other in the front-back direction L.

Preferably, the front external topsheet 70F, the front external backsheet 80F, the rear external topsheet 70R, and the rear external backsheet 80R each have a basis weight not exceeding 9 to 20 g/m$^2$. Preferably, a total basis weight of the front external topsheet 70F and the front external backsheet 80F is equal to or smaller than 32 g/m$^2$. Preferably, a total basis weight of the rear external topsheet 70R and the rear external backsheet 80R is equal to or smaller than 32 g/m$^2$. The external center sheet 100 connects the front external topsheet and backsheet 70F and 80F with the rear external topsheet and backsheet 70R and 80R in the front-back direction L. The external center sheet 100 may be located between the front external topsheet 70F and the absorber backsheet 30 or an elastic member covering sheet 43, and between the rear external topsheet 70R and the absorber backsheet 30 or the elastic member covering sheet 43. An elastic member 44 may be provided between the elastic member covering sheet 43 and the absorber. The external center sheet 100 prevents the absorbent body 1A from being uncovered. The external center sheet 100 can be made of, for example, air-through nonwoven fabric, spunbond nonwoven fabric, SMS nonwoven fabric, or a water-resistant film.

The front external backsheet 80F extends closer to the waist opening 8 than the front external topsheet 70F does. The front external backsheet 80F has a folded-back portion which is folded back at the waist opening 8. Specifically, the front external backsheet 80F is folded back toward the skin side of the wearer at the waist opening 8. The folded-back portion of the front external backsheet 80F is folded back to form a double overlapping region L1.

The rear external backsheet 80R extends closer to the waist opening 8 than the rear external topsheet 70R does. The rear external backsheet 80R has a folded-back portion which is folded back at the waist opening 8. Specifically, the rear external backsheet 80R is folded back toward the skin side of the wearer at the waist opening 8. The folded-back portion of the rear external backsheet 80R is folded back to form a double overlapping region L2.

The disposable diaper 1 has a reinforcing sheet 200A and a reinforcing sheet 200B in the front waist region S1 and the rear waist region S2, respectively. In the present embodiment, the reinforcing sheets 200A and 200B are provided on both front and rear waist regions S1 and S2. Alternatively, the reinforcing sheets may be provided on either the front waist region S1 or the rear waist region S2. Preferably, in this case, the reinforcing sheet is provided in the rear waist region S2.

The reinforcing sheets 200A and 200B may extend in a transverse direction W orthogonally crossing the front-back direction L. Preferably, the reinforcing sheets 200A and 200B continuously extend at least between the bonded portions 11 in the front waist region S1 and the rear waist region S2, respectively. The reinforcing sheets 200A and 200B overlap at least part of the folded-back portion of the front external backsheet 80F and the rear external backsheet 80R, respectively. Preferably, the reinforcing sheets 200A and 200B overlap the end portions of the absorber 40 in the front-back direction L closer to the skin side of the wearer than the absorber 40 is.

The reinforcing sheet 200A has a length L3 in the front-back direction L which is longer than the length L of the folded-back portion of the front external backsheet 80F in the front-back direction L. In this case, the reinforcing sheet 200A overlaps the tip end of the folded-back portion of the front external backsheet 80F in planar view. The reinforcing sheet 200B has a length L4 in the front-back direction L which is longer than the length L2 of the folded-back portion of the rear external backsheet 80R in the front-back direction L. In this case, the reinforcing sheet 200B overlaps the tip end of the folded-back portion of the rear external backsheet 80R in planar view. Preferably, the length of the reinforcing sheet 200B provided in the rear waist region S2 in the front-back direction L is longer than the length of the reinforcing sheet 200A provided in the front waist region S1 in the front-back direction L. Preferably, the length of the overlapping region of the reinforcing sheets 200A and 200B overlapping the front external backsheet 80F and the rear external backsheet 80R, respectively, is 5 to 15 mm in the front-back direction L.

In addition, from the viewpoint of preventing breakage, the exterior member 1B located closer to the waist opening 8 side than the regions of the reinforcing sheets 200A and 200B preferably has a maximum tensile strength equal to or larger than 25 [N/50 mm]. Preferably, a total maximum tensile strength of the exterior member 1B and the reinforcing sheets 200A and 200B in the regions where the reinforcing sheets 200A and 200B are disposed is equal to or larger than 35 [N/50 mm]. The exterior member 1B located closer to the leg openings 9 side than the regions of the reinforcing sheets 200A and 200B preferably has a maximum tensile strength equal to or larger than 15 [N/50 mm]. The maximum tensile strength is measured with Autograph tensile tester (Model: AG-1KNI) manufactured by SHIMADZU CORPORATION by fixing a sample having a width of 50 mm on a chuck at an inter-chuck distance of 100 mm and elongating the sample at a speed of 100 mm/min until the sample breaks. A used herein, "N/50 mm" indicates a tensile strength N per 50 mm width.

Preferably, the reinforcing sheets 200A and 200B are made of nonwoven fabric. The reinforcing sheets 200A and 200B may be made of, for example, polypropylene- or polyethylene-based nonwoven fabric, or nonwoven fabric including both polypropylene and polyethylene. The reinforcing sheets 200A and 200B may also be made of spunbond nonwoven fabric having a basis weight of, for example, 12 to 17 g/m$^2$. Alternatively, the reinforcing sheets 200A and 200B may be made of SMS nonwoven fabric preferably having a basis weight of 9 to 15 g/m$^2$, and more preferably 9 to 13 g/m$^2$. Preferably, the basis weight of the reinforcing sheets 200A and 200B is smaller than an average basis weight of the front external topsheet 70F, the rear external topsheet 70R, the front external backsheet 80F, and the rear external backsheet 80R.

Preferably, the reinforcing sheets 200A and 200B, the front external topsheet 70F, the rear external topsheet 70R, the front external backsheet 80F, and the rear external backsheet 80R are all made of nonwoven fabric.

Preferably, the reinforcing sheets 200A and 200B are disposed such that the portions having the largest tensile strength are arranged in the front-back direction L. Preferably, the reinforcing sheet 200A is intermittently bonded to at least either the front external topsheet 70F or the front external backsheet 80F. In other words, the surface of the reinforcing sheet 200A is preferably not entirely bonded. Preferably, the reinforcing sheet 200B is intermittently bonded to at least either the rear external topsheet 70R or the rear external backsheet 80R. In other words, the surface of reinforcing sheet 200B is preferably not entirely bonded. The reinforcing sheets 200A and 200B can be bonded with the exterior member 1B, for example, with a hot-melt adhesive or by sonic sealing.

Figure 4:
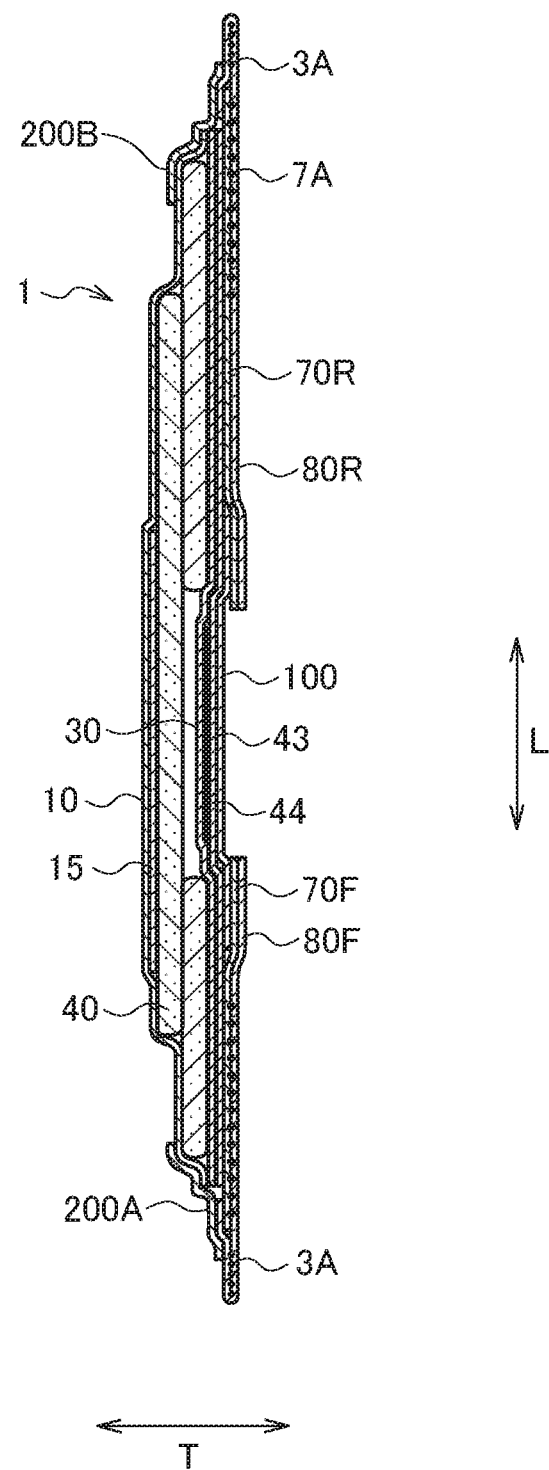
FIG. 4 is a cross-sectional view of a disposable diaper of FIG. 2 cut along line X2-X'2 according to another embodiment.

In the embodiment illustrated in FIG. 3, the end portions of the reinforcing sheets 200A and 200B on the waist opening 8 side in the front-back direction L are located inside the folded-back portions of the front external backsheet 80F and the rear external backsheet 80R, respectively. In this case, it is preferable to bond the reinforcing sheets 200A and 200B intermittently to the rear external backsheets 70R and 80R, respectively, by sonic sealing, and then bond the external topsheets 70F and 70R to the reinforcing sheets 200A and 200B with a hot-melt adhesive. Typically, bonding by sonic sealing often causes a loss of flexibility of the portions where fibers are fused and bonded. In this case, the external topsheets 70F and 70R do not include sonic-sealed portions, so that there is no portion where the sheet is locally hard. Besides, by intermittently applying the hot-melt adhesive, an excellent texture and air permeability can be achieved. Alternatively, as illustrated in FIG. 4, the reinforcing sheets 200A and 200B may be disposed closer to the skin side of the wearer than the folded-back portions of the front and rear external backsheets 80F and 80R are. In FIG. 4, the same reference signs are given to the parts similar to those of FIG. 3. Positions, lengths, materials, and the like of the reinforcing sheets 200A and 200B of FIG. 4 are similar to those of the embodiment of FIG. 3.

Waist gathers 3 and abdomen gathers 7 may be provided in the front waist region S1 and the rear waist region S2. The waist gathers 3 and the abdomen gathers 7 may respectively extend continuously from one edge of the front waist edge portion 4 to the other edge of the front waist edge portion 4' extending in the transverse direction W outside the absorbent article 1 in the front waist region S1, and from one side of the rear waist edge portion 6 to the other side of the rear waist edge portion 6' extending in the transverse direction W outside the absorbent article 1 in the rear waist region S2.

The waist gathers 3 and the abdomen gathers 7 each include a plurality of stretchable waist elastic members 3A and a plurality of abdomen elastic members 7A, respectively, in the transverse direction W. The waist elastic members 3A and the abdomen elastic members 7A extend in the transverse direction W. The plurality of waist elastic members 3A are provided closer to the waist opening 8 side than the plurality of abdomen elastic members 7A are. The waist elastic members 3A and the abdomen elastic members 7A are bonded to the exterior member 1B with the adhesive (e.g., hot-melt adhesive) in such a manner that the elastic members are elongated in the transverse direction W of the disposable diaper 1.

At least part of the waist elastic members 3A may be provided inside the folded-back portions of the front external backsheet 80F and/or the rear external backsheet 80R. The abdomen elastic members 7A are sandwiched between the front external topsheet 70F and the front external backsheet 80F, or between the rear external topsheet 80F and the rear external backsheet 80R.

Each member of the abdomen elastic members 7A is bonded to the external topsheets 70F and 70R and the external backsheets 80F and 80R with adhesives. There are portions in planar view where no adhesive is applied in the regions overlapping the reinforcing sheets 200A and 200B and among adhesives used to bond the abdomen elastic members 7A. In other words, the adhesive regions extending in the transverse direction W and the non-adhesive regions extending in the transverse direction W are disposed alternately in the front-back direction L.

Preferably, the pitch of the abdomen elastic members 7A in the front-back direction L is longer than the pitch of the waist elastic members 3A in the front-back direction L. The reinforcing sheets 200A and 200B may overlap at least part of the abdomen elastic members 7A in planar view.

The reinforcing sheets 200A and 200B may continuously extend in the front-back direction L. Alternatively, the reinforcing sheets 200A and 200B may intermittently extend in the front-back direction L. Preferably, in this case, an interval between the reinforcing sheets 200A and 200B in the front-back direction L is equal to or smaller than 5 mm. In particular, if the abdomen elastic members 7A are provided in the regions of the reinforcing sheets, it is possible to arrange the reinforcing sheets at intervals so as not to overlap the abdomen elastic members 7A just because the abdomen elastic members 7A themselves can yield a material strength. This decreases the amount of use of the reinforcing sheets 200A and 200B, while providing air permeability.

(2) Operation and Effect

The pants-type absorbent article 1 according to the present embodiment includes the external backsheets 80F and 80R that extend closer to the waist opening 8 than the external topsheets 70F and 70R are, and has the folded-back portions that are folded back at the waist opening 8. The reinforcing sheets 200A and 200B extend in the transverse direction W orthogonally crossing the front-back direction L and overlap at least part of the folded-back portions in planar view. The lengths L3 and L4 of the reinforcing sheets 200A and 200B, respectively, in the front-back direction L are longer than the lengths L1 and L2 of the folded-back portions in the front-back direction L. The wearer can easily grab the folded-back portions located in the front and rear waist regions S1 and S2. Accordingly, the folded-back portions tend to receive pressure of fingers of the wearer when worn and while the wearer is active. Thus, the regions near the folded-back portions can be easily torn particularly when worn and while the wearer is active. In particular, the exterior member 1B tears more easily as the thickness of the exterior member 1B decreases.

The present embodiment improves the strength of the easily-tearable regions with the reinforcing sheets 200A and 200B that overlap at least part of the folded-back portions. Meanwhile, the lengths L3 and L4 of the reinforcing sheets 200A and 200B in the front-back direction L are longer than the lengths L and L2 of the folded-back portions in the front-back direction L, so that the reinforcing sheets 200A and 200B overlap the tip ends of the external backsheets 80F and 80R, respectively, in the front-back direction L. Thus, the reinforcing sheets 200A and 200B can protect the tip ends of the folded-back portions which tend to be broken very easily. Even when the exterior member 1B is made thinner, the breakage can be prevented when worn and while the wearer is active.

According to one embodiment, the total basis weight of the external topsheets 70F and 70R and the external backsheets 80F and 80R is equal to or smaller than 32 g/m$^2$. This improves flexibility of at least either front or rear waist region S1, S2. Such a low basis weight can also lead to the decrease of a manufacturing cost. Even when the total basis weight is not more than 32 g/m$^2$, the breakage of the absorbent article 1 can be prevented, because the reinforcing sheets 200A and 200B can increase the strength of at least the front waist region S1 or the rear waist region S2.

According to one embodiment, the reinforcing sheet 200A or 200B is provided at least in the rear waist region S2. When the wearer tries to put on the pants-type absorbent article 1, the buttocks of the wearer may be stuck in the absorbent article 1. In such a case, the wearer grabs and tries to strongly pull up the rear waist region S2. The present embodiment can prevent breakage of the absorbent article 1 when worn, because the reinforcing sheet 200A or 200B is provided in the rear waist region S2.

According to one embodiment, the reinforcing sheets 200A and 200B are provided in both front and rear waist regions S1 and S2. The length L4 of the reinforcing sheet 200B in the rear waist region S2 in the front-back direction L is longer than the length L3 of the reinforcing sheet 200A in the front waist region S1 in the front-back direction L. When the buttocks of the wearer are stuck in the absorbent article 1, the wearer often tries to pull up the absorbent article 1 while grabbing the rear waist region S2 longitudinally in the front-back direction L, to pull up the rear waist region S2. In such a case, the breakage of the absorbent article 1 can further be prevented when worn, because the length L4 of the reinforcing sheet 200B in the rear waist region S2 is relatively long in the front-back direction L.

According to one embodiment, the reinforcing sheets 200A and 200B overlap the end portions of the absorber 40 in the front-back direction L closer to the skin side of the wearer than the absorber 40 is. The absorber 40 is a portion having a relatively high rigidity in the absorbent article 1. Accordingly, the end portions of the absorber 40 easily give a relatively strong stimulus to the skin of the wearer. In the present embodiment, such a stimulus to the skin of the wearer by the end portions of the absorber 40 can be reduced because the reinforcing sheets 200A and 200B cover the end portions of the absorber 40.

According to one embodiment, the reinforcing sheets 200A and 200B are made of nonwoven fabric and intermittently bonded to at least either the external topsheet 70F or 70R, or the external backsheet 80F or 80R. Since the reinforcing sheets 200A and 200B made of nonwoven fabric are bonded intermittently and not entirely, the front waist region S1 and/or the rear waist region S2 can have flexibility and air permeability.

According to one embodiment, the end portions of the reinforcing sheets 200A and 200B are located inside the folded-back portions in the front-back direction L. If the end portions, especially the unbonded end portions of the sheets, come to touch the skin of the wearer, the wearer would have unreliable feeling. In the present embodiment, the end portion of at least either the reinforcing sheet 200A or 200B is located inside the folded-back portion. This prevents the end portions of the reinforcing sheets 200A and 200B located inside the folded-back portions from directly contacting the skin of the wearer. This eliminates unreliable feeling to the wearer.

According to one embodiment, the pants-type absorbent article 1 further includes the abdomen elastic members 7A sandwiched between the external topsheets 70F and 70R and the external backsheets 80F and 80R and extend in the transverse direction W orthogonally crossing the front-back direction L. The abdomen elastic members 7A in the front and rear waist regions S1 and S2 can prevent slippage of the pants-type absorbent article 1 from the wearer.

According to one embodiment, the pants-type absorbent article 1 further includes the waist elastic members 3A provided inside the folded-back portions closer to the waist opening 8 side than the abdomen elastic members 7A are and extend in the transverse direction W. The pitch of the abdomen elastic members 7A in the front-back direction L is longer than the pitch of the waist elastic members 3A in the front-back direction L. The reinforcing sheets 200A and 200B overlap at least part of the abdomen elastic members 7A in planar view. When the wearer tries to put on the absorbent article 1, the fingers of the wearer tend to enter the portions having a wide pitch among the elastic members 3A and 7A. In the present embodiment, the fingers of the wearer are easily put into the regions between adjacent abdomen elastic members 7A. Even when the fingers or nails of the wearer are stuck, the reinforcing sheets 200A and 200B are provided in this region, the absorbent article 1 does not easily tear.

According to one embodiment, the reinforcing sheets 200A and 200B may overlap at least part of the abdomen elastic members 7A in planar view. Each member of the abdomen elastic members 7A is bonded to the external topsheets 70F and 70R and the external backsheets 80F and 80R with adhesives. There are portions in planar view where no adhesive is applied in the regions overlapping the reinforcing sheets 200A and 200B and among adhesives used to bond the abdomen elastic members 7A. If a large amount of adhesive is applied, the flexibility of the absorbent article 1 would be decreased. In the present embodiment, the regions with no adhesive applied thereto are provided between adjacent abdomen elastic members 7A in the front-back direction L, so that the regions between adjacent abdomen elastic members 7A can have flexibility. Further, the reinforcing sheets 200A and 200B cover the regions where no adhesive is applied between adjacent abdomen elastic members 7A, allowing improvement of the strength of such regions.

Although the embodiments of the present invention have been described above in detail, it is apparent for persons who have ordinary skill in the art that the embodiments described in this disclosure do not limit the scope of the present invention. Changes and modifications may apply to the embodiments of the present invention without departing from the spirit and scope of the present invention that are defined by the description of the appended claims. The description of the present disclosure, therefore, has been understood to be illustrative and is in no way intended to limit the scope of the invention.

The entire contents of Japanese Patent Application No. 2015-116118 (filed on Jun. 8, 2015) have been incorporated herein by reference.

INDUSTRIAL APPLICABILITY

The pants-type absorbent article according to the embodiment described above can decrease the breakage of the pants-type absorbent article when worn and the wearer is active.

REFERENCE SIGNS LIST 1 disposable diaper (absorbent article)
1A absorbent body
1B exterior member
3A waist elastic member
4,4' front waist edge portion
6,6' rear waist edge portion
7A abdomen elastic member
8 waist opening
40 absorber
70F front external topsheet
70R rear external topsheet
80F front external backsheet
80R rear external backsheet
S1 front waist region
S2 rear waist region
S3 crotch region
L front-back direction
W transverse direction

The invention claimed is:

1. A pants-type absorbent article, comprising:
a front waist region to be placed on a front waist of a wearer;
a rear waist region to be placed on a rear waist of the wearer;
a crotch region located between the front waist region and the rear waist region;
a front-back direction extending from the front waist region to the rear waist region;
a waist opening defined by the front waist region and the rear waist region and disposed to surround a waist of the wearer;
an external topsheet provided on at least one of the front waist region and the rear waist region; and
an external backsheet bonded to the external topsheet, wherein
the external backsheet has a folded-back portion folded back at the waist opening, the folded-back portion extending beyond the external topsheet toward to the waist opening,
a reinforcing sheet is provided to extend in a transverse direction orthogonally crossing the front-back direction and to overlap at least part of the folded-back portion,
the reinforcing sheet has a length in the front-back direction longer than a length of the folded-back portion in the front-back direction,
the reinforcing sheet is provided in both the front waist region and the rear waist region, and
the reinforcing sheet provided in the rear waist region has a length in the front-back direction longer than a length of the reinforcing sheet provided in the front waist region.

2. The pants-type absorbent article according to claim 1, wherein
a total basis weight of the external topsheet and the external backsheet is equal to or smaller than 32 g/m$^2$.

3. The pants-type absorbent article according to claim 1, wherein
the reinforcing sheet is provided at least in the rear waist region.

4. The pants-type absorbent article according to claim 1, further comprising an absorber disposed at least in the crotch region, wherein
the reinforcing sheet overlaps an end portion of the absorber in the front-back direction on a skin side of the wearer than the absorber.

5. The pants-type absorbent article according to claim 1, wherein the reinforcing sheet is made of nonwoven fabric and is bonded intermittently to at least one of the external topsheet and the external backsheet.

6. The pants-type absorbent article according to claim 1, wherein an end portion of the reinforcing sheet is located inside the folded-back portion in the front-back direction.

7. The pants-type absorbent article according to claim 1, further comprising:

a plurality of abdomen elastic members sandwiched between the external topsheet and the external backsheet, the abdomen elastic members extending in the transverse direction orthogonally crossing the front-back direction.

8. The pants-type absorbent article according to claim 7, further comprising:

a plurality of waist elastic members provided inside the folded-back portion closer to the waist opening side than the abdomen elastic members, the waist elastic members extending in the transverse direction, wherein a pitch of the abdomen elastic members in the front-back direction is longer than a pitch of the waist elastic members in the front-back direction, and the reinforcing sheet overlaps at least part of the abdomen elastic members in planar view.

9. The pants-type absorbent article according to claim 7, wherein the reinforcing sheet overlaps at least part of the abdomen elastic members in planar view, each of the abdomen elastic members is bonded to the external topsheet and the external backsheet with adhesives, and a region where no adhesive is applied in planar view is provided in the region overlapping the reinforcing sheet and between the adhesives for bonding the abdomen elastic members.

* * * * *